US00PP11187P

United States Patent [19]

Glicenstein

[11] Patent Number: Plant 11,187

[45] Date of Patent: Jan. 25, 2000

[54] AZALEA PLANT NAMED 'IRISH LACE'

[75] Inventor: Leon Glicenstein, State College, Pa.

[73] Assignee: Yoder Brothers, Inc., Barberton, Ohio

[21] Appl. No.: 09/080,949

[22] Filed: May 20, 1998

[51] Int. Cl.[7] ..... A01H 5/00

[52] U.S. Cl. ..... Plt./238

[58] Field of Search ..... Plt./238, 239, 240

*Primary Examiner*—Howard J. Locker
*Assistant Examiner*—Kent L. Bell
*Attorney, Agent, or Firm*—C. A. Whealy

[57] ABSTRACT

A new and distinct cultivar of Azalea plant named 'Irish Lace', characterized by its very dark green leaves that do not abscise during the cooling and forcing periods; dense, uniform and symmetrical plant habit; rapid flowering after forcing; numerous greenish-white-colored flowers with undulating petal margins which give the flowers a ruffled appearance; single to semi-double hose-in-hose flower form; and excellent postproduction longevity with plants maintaining good flower substance for up to four weeks in an interior environment.

1 Drawing Sheet

BACKGROUND OF THE INVENTION

The present invention relates to a new and distinct cultivar of Azalea, botanically known as *Rhododendron hybrida,* an evergreen greenhouse-forcing type, and hereinafter referred to by the name 'Irish Lace'.

The new Azalea is a product of a planned breeding program conducted by the inventor in Alva, Fla. The objective of the breeding program is to create new Azalea varieties having uniform plant habit and uniform flowering, numerous flowers, good foliage retention during the cooling and forcing periods, and excellent postproduction longevity.

The new Azalea originated from a cross made by the inventor in Alva, Fla., of the non-patented commercial cultivar 'Jacinth' as the female, or seed, parent with the commercial cultivar 'Solitaire' (disclosed in U.S. Plant Pat. No. 3,171) as the male, or pollen, parent.

Compared to plants of the dark pink, double-flowered cultivar 'Jacinth', plants of the new Azalea are more vigorous, have better foliage retention, and have greenish-white single to semi-double hose-in-hose flowers.

In addition to flower color, plants of the new Azalea are more uniform, symmetrical and compact than plants of the pink-flowered cultivar 'Solitaire'. Additionally, plants of the new Azalea have more ruffled petal margins than plants of the cultivar 'Solitaire' and resist leaf curl that is occasionally observed on plants of the cultivar 'Solitaire'.

The new Azalea was discovered and selected by the inventor as a flowering plant within the progeny of the stated cross in a controlled environment in Alva, Fla., on Sep. 28, 1994. The selection of this plant was based on its desirable flower color, profuse and uniform flowering, improved foliage retention, uniform plant habit and good postproduction longevity.

Asexual reproduction of the new Azalea by terminal cuttings taken in a controlled environment in Alva, Fla., has shown that the unique features of this new Azalea are stable and reproduced true to type in successive generations.

The new Azalea has not been observed under all possible environmental conditions. The phenotype may vary somewhat with variations in environment such as temperature, daylength, light intensity, nutrition and water status without, however, any variance in genotype.

BRIEF SUMMARY OF THE INVENTION

The following traits have been repeatedly observed and are determined to be the unique characteristics of 'Irish Lace'. These characteristics in combination distinguish 'Irish Lace' as a new and distinct cultivar:

1. Very dark green leaves that do not abscise during the cooling and forcing periods.

2. Dense, uniform and symmetrical plant habit.

3. Rapid flowering after forcing.

4. Numerous greenish-white-colored flowers with undulating petal margins which give the flowers a ruffled appearance.

5. Single to semi-double hose-in-hose flower form.

6. Excellent postproduction longevity with plants maintaining good flower substance for up to four weeks in an interior environment.

Plants of the new Azalea can be compared to plants of the white-flowered cultivar 'White Gish' (not patented). However, in side-by-side comparisons conducted in Alva, Fla., plants of the new Azalea differ from plants of the cultivar 'White Gish' in the following characteristics:

1. After forcing, plants of the new Azalea flower about 11 to 14 days faster than plants of the cultivar 'White Gish'.

2. Flowers of plants of the new Azalea are less double than flowers of plants of the cultivar 'White Gish'.

3. Flowers of plants of the new Azalea have a more greenish-white color compared to flowers of plants of the cultivar 'White Gish'.

4. Plants of the new Azalea have better foliage retention than plants of the cultivar 'White Gish'.

5. Plants of the new Azalea last about five days longer than plants of the cultivar 'White Gish'.

Plants of the new Azalea can also be compared to plants of the white-flowered cultivar 'White Dogwood' (not patented). However, in side-by-side comparisons conducted in Alva, Fla., plants of the new Azalea differ from plants of the cultivar 'White Dogwood' in the following characteristics:

1. Plants of the new Azalea are more spreading compared to the upright plant habit of plants of the cultivar 'White Dogwood'.

2. Leaves of plants of the new Azalea are glossier than leaves of plants of the cultivar 'White Dogwood'.

3. Flowers of plants of the new Azalea are single to semi-double hose-in-hose whereas flowers of plants of the cultivar 'White Dogwood' are single.

4. Flowers of plants of the new Azalea do not shatter whereas flowers of plants of the cultivar 'White Dogwood' shatter and are not persistent.

BRIEF DESCRIPTION OF THE PHOTOGRAPHS

The accompanying colored photographs illustrate the overall appearance of the new Azalea, showing the colors as true as it is reasonably possible to obtain in colored reproductions of this type.

The photograph at the top of the sheet comprises a side perspective view of a typical plant of 'Irish Lace'.

The photograph at the bottom of the sheet is a close-up view of a typical flower of 'Irish Lace'. Flower and foliage colors in the photographs may appear different from the actual colors due to light reflectance.

DETAILED BOTANICAL DESCRIPTION

The aforementioned and following observations, measurements, values, and comparisons describe plants grown in Alva, Fla., in 12.5-cm containers with day temperatures ranging from 16 to 35° C. and night temperatures ranging from 10 to 24° C. Plants were grown under 50 percent polypropylene shade cloth reducing ambient light levels to about 4,000 to 5,000 footcandles. After flower bud development, plants were cooled at 3 to 5° C. for six weeks to break flower bud dormancy. Plants were subsequently forced into flower under commercial conditions in a polyethylene-covered greenhouse.

In the following description, color references are made to The Royal Horticultural Society Colour Chart except where general terms of ordinary dictionary significance are used.

Botanical classification:

*Botanical.*—*Rhododendron hybrida* 'Irish Lace'.

*Commercial.*—Evergreen greenhouse-forcing type Azalea.

Parentage:

*Male or pollen parent.*—*Rhododendron hybrida* 'Solitaire', disclosed in U.S. Plant Pat. No. 3,171.

*Female or seed parent.*—*Rhododendron hybrida* 'Jacinth', not patented.

Propagation:

*Type.*—By terminal cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Rooting habit.*—Moderately vigorous and finely-branched.

Plant description:

*Plant form and growth habit.*—Perennial, evergreen, upright and outwardly spreading, inverted triangle, uniform and symmetrical plant habit. Moderate vigor. Numerous flowers per plant.

*Branching habit.*—Moderate branching, about three or four lateral branches develop after removal of terminal apex.

*Plant height, soil level to top of flowers.*—About 23 cm.

*Plant diameter, area of spread.*—About 38 cm.

*Lateral branch description.*—Length: About 24 cm. Diameter: About 5 mm. Color: Immature: 144B/144C. Mature: Woody, lighter than 165A. Texture: Pubescent.

Foliage description:

*Arrangement.*—Alternate, single.

*Length.*—About 4.5 cm.

*Width.*—About 2.2 cm.

*Shape.*—Elliptic.

*Apex.*—Mucronate.

*Base.*—Cuneate.

*Margin.*—Entire.

*Texture.*—Leathery, pubescent on both surfaces.

*Color.*—Young foliage, upper surface: Dark green, darker than 147A. Young foliage, lower surface: Close to 147B. Mature foliage, upper surface: Much darker than 147A. Mature foliage, lower surface: Close to 147B.

*Petiole.*—Length: About 6.5 mm. Diameter: About 2 mm. Color: 144B/144C.

Flower description:

*Natural flowering season.*—Spring after sufficient cool period.

*Time to flower* (*Forcing period*).—After about four to six weeks of cooling at 4 to 9° C. plants will typically require an additional three to five weeks to develop about 12 colored flower buds.

*Flower arrangement.*—Flowers arranged singly at terminals with usually about four flowers per apex. Flowers face upward and outward. Very freely flowering.

*Flower appearance.*—Medium-sized star-shaped single to semi-double hose-in-hose. White-colored petals with greenish throat gives a greenish-white overall appearance to the flowers. Flowers persistent.

*Flower diameter.*—About 7.5 cm.

*Postproduction longevity.*—Under interior conditions, plants maintain good flower substance for about four weeks.

*Flower bud* (*just starting to show petal color*).—Rate of opening: About three days depending on temperatures. Length: About 1.3 cm. Diameter: About 1 cm. Shape: Ovoid. Color: 145B.

*Petals/sepals.*—Appearance: Satiny. Texture: Smooth. Arrangement: Single to semi-double, bose-in-hose. Calyx may be fully developed and transformed into petals. Corolla usually consists of five fused petals with up to five stamenoidal petaloids. Shape: Spatulate with rounded apex. Margin: Margin occasionally indented, undulating edge gives a ruffled appearance. Corolla length: About 4.6 cm. Corolla lobe width: About 2.6 cm. Calyx length: About 4 cm. Calyx lobe width: About 2.8 cm. Color: When opening and fully opened, upper and lower surfaces: Iridescent, 155D. Throat: Tinged with light green, fainter than 144C.

*Peduncles.*—Length: About 1.4 cm. Diameter: About 2 mm. Angle: Upright. Strength: Flexible, but strong. Texture: Pubescent. Color: 144A/144B.

*Reproductive organs.*—Androecium: Stamen number: Five to ten partially transformed petaloids. Stamen length: About 2.5 cm. Anther shape: Oblong. Anther size: About 3 mm by 1 mm. Anther color: Close to 167A. Amount of pollen: Moderate to low. Gynoecium: Pistil length: About 3.25 cm. Stigma shape: Rounded. Stigma color: Green. Style color: White. Ovary color: Light green, heavily whiskered.

Disease resistance: No known Azalea diseases observed to date on plants grown under commercial greenhouse conditions.

Seed production: Seed production has not been observed.

It is claimed:

1. A new and distinct Azalea plant named 'Irish Lace', as illustrated and described.

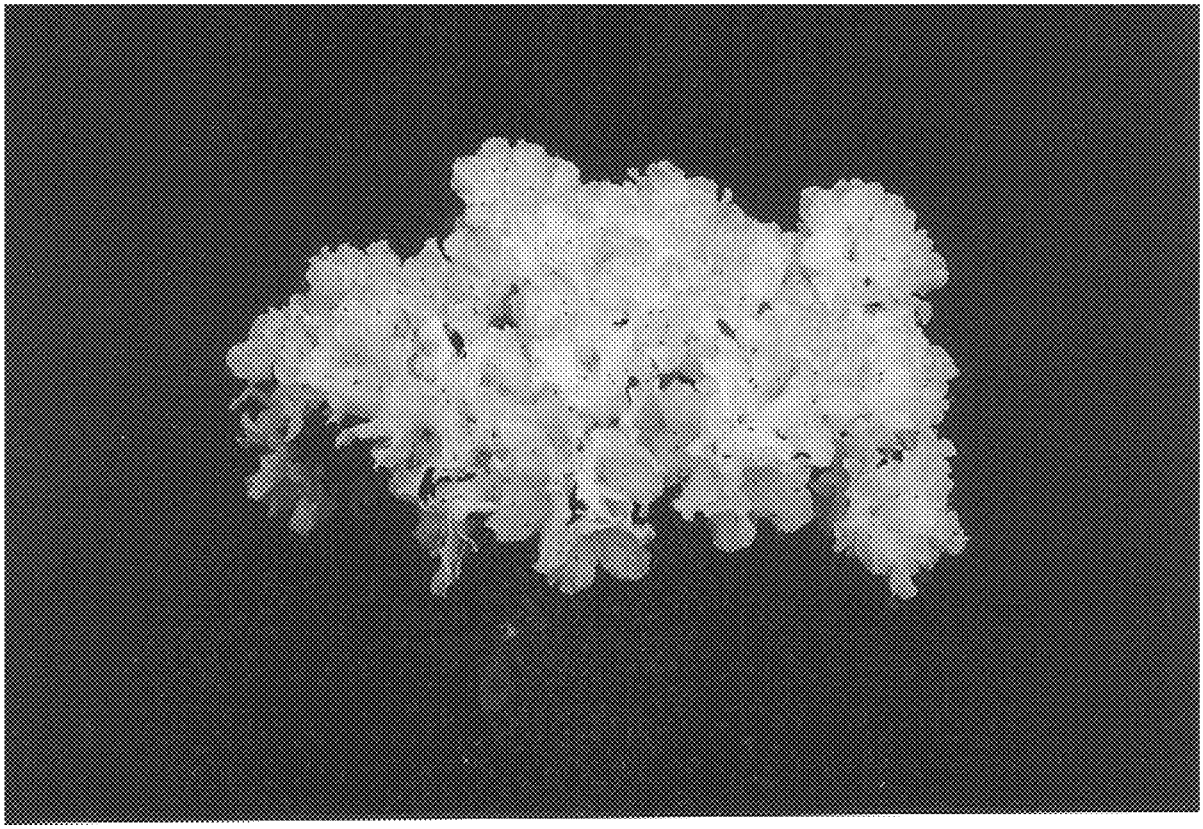
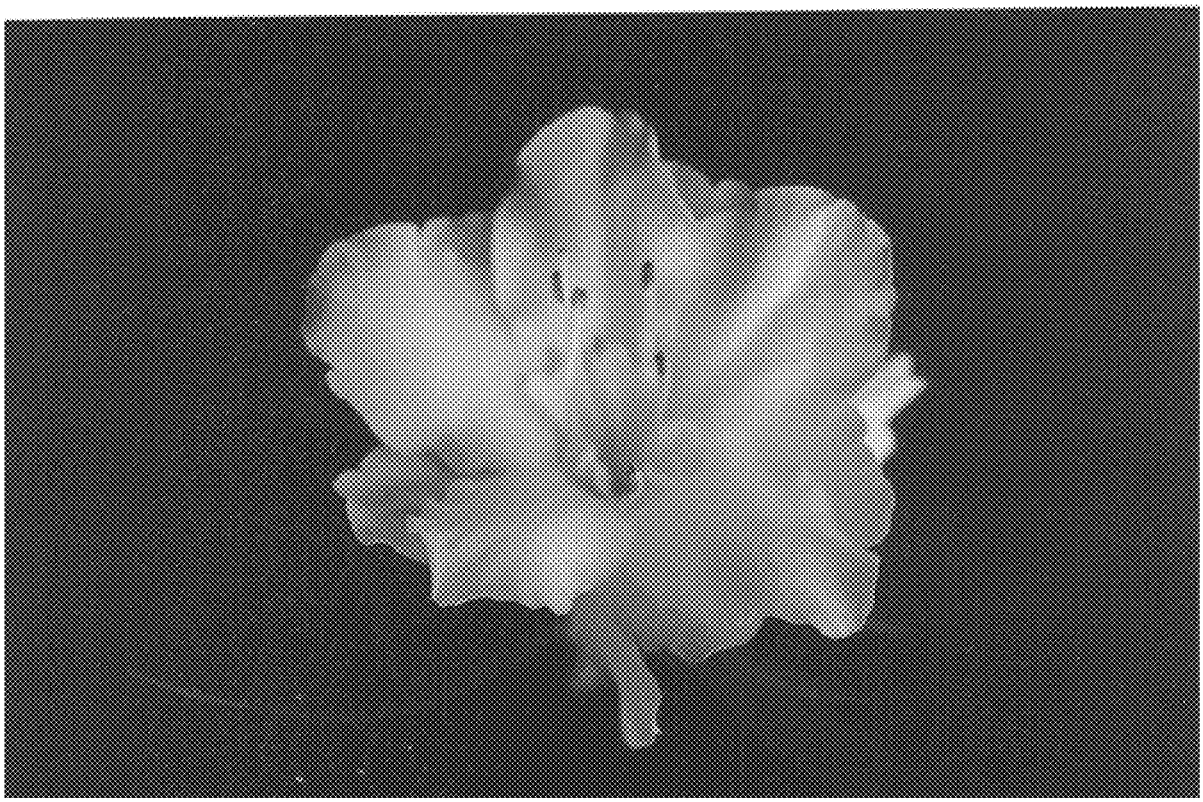

* * * * *